United States Patent
Chen et al.

(10) Patent No.: US 10,697,924 B2
(45) Date of Patent: Jun. 30, 2020

(54) GAS SENSOR FOR DETECTING HYDROCARBONS

(71) Applicant: Carrier Corporation, Farmington, CT (US)

(72) Inventors: Lei Chen, South Windsor, CT (US); Zhiwei Yang, South Windsor, CT (US); Antonio M. Vincitore, South Windsor, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 10 days.

(21) Appl. No.: 15/505,012

(22) PCT Filed: Aug. 20, 2015

(86) PCT No.: PCT/US2015/046090
§ 371 (c)(1),
(2) Date: Feb. 17, 2017

(87) PCT Pub. No.: WO2016/029003
PCT Pub. Date: Feb. 25, 2016

(65) Prior Publication Data
US 2018/0195995 A1 Jul. 12, 2018

Related U.S. Application Data

(60) Provisional application No. 62/039,785, filed on Aug. 20, 2014.

(51) Int. Cl.
*G01N 27/407* (2006.01)
*G01N 33/00* (2006.01)

(52) U.S. Cl.
CPC ..... *G01N 27/4074* (2013.01); *G01N 27/4075* (2013.01); *G01N 33/0047* (2013.01)

(58) Field of Classification Search
CPC ............... G01N 27/406–4078; G01N 33/0047
See application file for complete search history.

(56) References Cited

U.S. PATENT DOCUMENTS

| 3,852,169 A | 12/1974 | Kring et al. |
| 4,012,991 A | 3/1977 | Olson et al. |
| (Continued) | | |

FOREIGN PATENT DOCUMENTS

| CN | 1236100 A | 11/1999 |
| CN | 201464362 U | 5/2010 |
| (Continued) | | |

OTHER PUBLICATIONS

International Preliminary Report on Patentability regarding related PCT App. No. PCT/US2015/046090, dated Mar. 2, 2017; 10 pgs.

(Continued)

*Primary Examiner* — J. Christopher Ball
(74) *Attorney, Agent, or Firm* — Cantor Colburn LLP

(57) ABSTRACT

A gas sensor includes a housing (22) having disposed therein a membrane electrode assembly comprising a sensing electrode (14), a counter electrode (16), and a solid polymer electrolyte (12) disposed between the sensing electrode and the counter electrode. The sensing electrode comprises a first catalyst comprising noble metal nanoparticles (34). The counter electrode comprises a second catalyst comprising noble metal nanoparticles (34), which can be of the same composition or a different composition as the first catalyst. The sensor housing also includes an opening (24) in fluid communication with the sensing electrode for test gas to contact the sensing electrode. The sensor also includes an electrical circuit (19) connecting the sensing electrode and the counter electrode.

16 Claims, 2 Drawing Sheets

(56) References Cited

U.S. PATENT DOCUMENTS

| | | |
|---|---|---|
| 4,511,659 A | 4/1985 | Matson |
| 4,591,414 A | 5/1986 | Zaromb et al. |
| 4,707,242 A | 11/1987 | Schneider et al. |
| 5,173,166 A | 12/1992 | Tomantschger et al. |
| 5,266,309 A | 7/1993 | Stetter et al. |
| 5,302,274 A * | 4/1994 | Tomantschger ... G01N 27/4045 204/412 |
| 5,448,905 A | 9/1995 | Stetter et al. |
| 6,238,535 B1 | 5/2001 | Taniguchi et al. |
| 7,858,262 B2 * | 12/2010 | Faucheux ............ H01M 8/006 429/519 |
| 8,070,355 B2 | 12/2011 | Minor et al. |
| 2003/0085125 A1 * | 5/2003 | Prohaska ........... G01N 27/4071 204/424 |
| 2006/0091022 A1 | 5/2006 | Ruud et al. |
| 2007/0102294 A1 | 5/2007 | Dorisio Deininger et al. |
| 2008/0280190 A1 | 11/2008 | Dopp et al. |
| 2008/0295580 A1 | 12/2008 | Minor et al. |
| 2011/0207019 A1 | 8/2011 | Mukerjee |
| 2012/0125772 A1 | 5/2012 | Stetter et al. |
| 2013/0153442 A1 | 6/2013 | Chen et al. |

FOREIGN PATENT DOCUMENTS

| | | |
|---|---|---|
| EP | 2639577 A1 | 9/2013 |
| WO | 2007020410 A1 | 2/2007 |

OTHER PUBLICATIONS

Chinese Office Action from the Chinese Patent Office for CN Application No. 201580057160.2 dated Nov. 1, 2018, 22 pages, English Translation Included.

* cited by examiner

GAS SENSOR FOR DETECTING HYDROCARBONS

CROSS-REFERENCES TO RELATED APPLICATIONS

This is a national stage of International Patent Application Serial No. PCT/US2015/046090, filed Aug. 20, 2015, which claims the benefit of U.S. provisional application No. 62/039,785, filed Aug. 20, 2014, both of which are incorporated herein by reference in their entirety.

BACKGROUND

Gas sensors for detecting hydrocarbons or substituted hydrocarbons have been used in various industrial or laboratory settings for process control. As the compounds can also be flammable or explosive, gas detection sensors have also been used for leak detection where such compounds are used or manufactured. Various types of sensors have been used or proposed. Examples include metal oxide semiconductor (MOS) sensors, non-dispersive infrared detector (NDIR) sensors, pellistor (pelletized resistor) sensors, and mixed potential utilizing high-temperature solid electrolytes made of ceramic such as perovskite.

New applications for hydrocarbons or substituted hydrocarbons have created and continue to create new challenges for gas detection sensors. One such application is in the field of cooling and heating, where older chlorinated hydrocarbons (CFCs) were eliminated due to their adverse impact on the earth's ozone layer. Chlorinated fluorocarbons were initially replaced with chlorofluorocarbons R12 (dichlorodifluoroethane); however, continued concerns with their ozone depleting potential (ODP) and new concerns with the compounds' global warming potential (GWP) led to their replacement with fluorinated hydrocarbons like R32. Continued concerns with ODP and GWP, coupled with performance requirements in vapor compression heat transfer systems, have led to the development of new refrigerants such as fluorinated unsaturated hydrocarbons (i.e., fluorinated olefins) like trans-1,333-tetrafluoropropene (R1234ze). However, since refrigerant flow loops in many HVAC and refrigeration systems are at least partially located in interior building spaces, concerns with toxicity and/or flammability risks arising from leaks have created an expanded need for effective gas detection for such compounds. In many areas, building codes are being developed that will mandate such gas detection capability.

The above types of sensors have been used with varying degrees of success in the industrial or laboratory settings where they have been employed. However, many such sensors have limitations that can impact their effectiveness in demanding new and existing applications. For example, MOS and pellistor sensors are prone to false alarms due to cross-sensitivity. Additionally, durability of MOS sensors for detection of fluorinated hydrocarbons is questionable, as HF could be generated that could potentially damage the sensors. NDIR sensors have been used in low-volume applications, but difficult and expensive to manufacture to appropriate tolerances required by the residential HVAC market, and are likely unsuitable for widespread implementation as is anticipated for HVAC and refrigeration systems. As implied by the name, high temperature solid electrolyte systems require high temperatures (typically in excess of 500° C.) that render them impractical for many applications such as residential and commercial HVAC and refrigeration systems in terms of cost and lifetime constraints.

In view of the demanding requirements for hydrocarbon gas sensor, there remains a need for new alternatives that may be more appropriate for or function better in certain environments, offer better cost, or enable beneficial modifications to the overall sensor design.

BRIEF DESCRIPTION

According to some aspects of the disclosure, a gas sensor includes a housing having disposed therein a membrane electrode assembly comprising a sensing electrode, a counter electrode, and a solid polymer electrolyte disposed between the sensing electrode and the counter electrode. The sensing electrode comprises a first catalyst comprising noble metal nanoparticles. The counter electrode comprises a second catalyst comprising noble metal nanoparticles, which can be of the same composition or a different composition as the first catalyst. The sensor housing also includes an opening in fluid communication with the sensing electrode for test gas to contact the sensing electrode. The sensor also includes an electrical circuit connecting the sensing electrode and the counter electrode.

According to some aspects of the disclosure, a method of using the above-described sensor comprises applying a positive bias voltage to the sensing electrode relative to the counter electrode or a reference electrode. A test gas is then brought into contact with the sensing electrode, and an electrochemical response voltage or current in the electrical circuit connecting the sensing electrode and the counter electrode is generated from oxidation of hydrocarbons or substituted hydrocarbons at the sensing electrode. This electrochemical response voltage or current is measured to determine the presence and/or concentration of the tested hydrocarbon(s) or substituted hydrocarbon(s) in the test gas.

BRIEF DESCRIPTION OF THE DRAWINGS

Subject matter of this disclosure is particularly pointed out and distinctly claimed in the claims at the conclusion of the specification. The foregoing and other features, and advantages of the present disclosure are apparent from the following detailed description taken in conjunction with the accompanying drawings in which:

DETAILED DESCRIPTION

Figure 1:
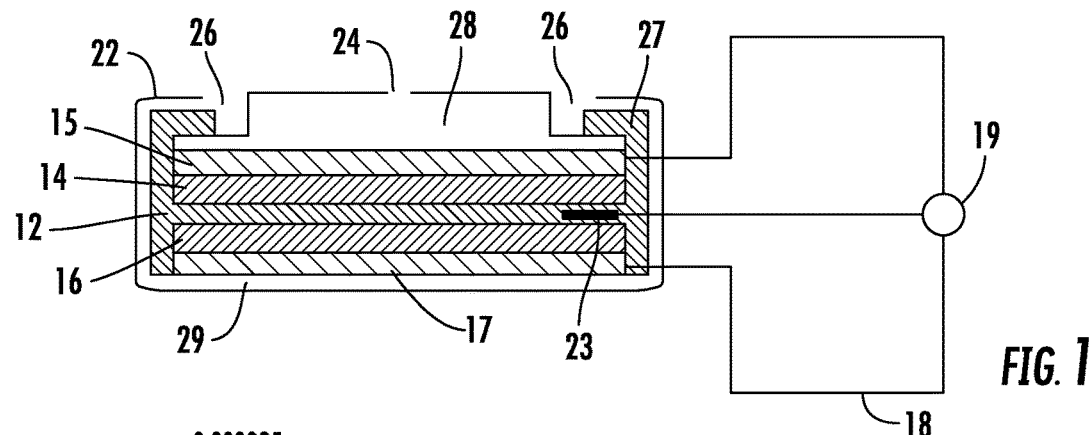
FIG. 1 depicts a simplified schematic representation of a gas sensor as described herein.

A gas sensor is schematically shown in FIG. 1, in which a membrane electrode assembly (MEA) has a solid polymer electrolyte (SPE) (i.e., ion conducting polymer) 12 disposed between sensing electrode 14 and counter electrode 16. Current collectors 15 and 17 are attached to the electrodes and are connected to circuit 18, which includes measurement and/or control device 19. In some embodiments, an optional reference electrode 23 can be disposed in the SPE 12 at a location between the sensing electrode 14 and the counter electrode 16. The current collectors 15, 17 can be formed from a conductive mesh or felt, and are depicted with thickness so that they can also function as gas diffusion media for test gas and reference gas to reach the surface of the electrodes 14, 16. In other embodiments, the current collectors 15, 17 can be relatively thin, almost 2-dimensional conductive screens on the surface of the electrodes 14, 16 with adjacent gas diffusion media that does not have to be conductive. The current collector/gas diffusion medium 15 associated with the sensing electrode 14 can be formed from an oxidation-resistant material such as graphitized carbon or stainless steels. The current collector/gas diffusion medium 17 can be formed from a conductive material such as carbon. Measurement and/or control device 19 can be a voltmeter or ampere meter, but in many cases comprises a potentiostatic circuit, microprocessor, or similar electronic device with integrated voltage and or amperage measurement functions and also can apply a voltage bias between the sensing electrode 14 and counter electrode 16 during operation of the sensor.

A housing 22 is disposed around the MEA, having an opening 24 to allow a test gas to enter the sensor with the flux of gas regulated by the size of the opening. The opening is shown as completely open, although it is understood that they may be covered with a screen or gas permeable membrane or an adsorber. Also, opening 24 is shown for purposes of illustration as leading directly into chamber 28 for the test gas, but the gas may also be introduced into interior chambers through channel(s) that lead from an outer surface of the sensor to interior chambers. The edges of the electrode assembly membrane can be sealed against seal 27 formed of a seal material such as rubber so that the test gas is kept on the sensing electrode side of the MEA, although other techniques known in the art (e.g., disposing the MEA in a frame (not shown) that is sealed to the edges of the housing) can be used. Though the seal prevents the test gas from entering the counter electrode side, it was found that even with passage of the test gas into the counter electrode side, the sensor can still function properly to determine the presence of hydrocarbons or substituted hydrocarbons. Accordingly, the counter electrode 16 can also be exposed to the test gas from a passage 29 leading from opening 24 or from another opening 26 in the housing 22. The electrodes 14, 16 can be bonded to the solid polymer electrolyte as depicted in FIG. 1, but can also be held together by other means such as mechanical clamping force without compromising the functionalities of the sensor.

Of course, the embodiment depicted in FIG. 1 is schematic and exemplary in nature, and other configurations can be used as well. Exemplary gas sensor configurations and variations thereon are disclosed, for example, in U.S. Pat. Nos. 5,650,054, 5,573,648, 6,200,443, 6,948,352, US 2009/0184005 A1, and US 2010/0012494 A1, the disclosures of which are incorporated herein by reference in their entirety.

Although the disclosure is not bound by any theory or perceived mechanism of operation, electrochemical oxidation of hydrocarbons such as olefins is believed to take place via a two one-electron process as shown in equations (1a) and/or (1b) below (exemplified with propene), with concomitant reaction at the counter electron as shown in equation (2):

$$CH_3CH=CH_2+2H_2O-2e^- \rightarrow CH_3CH(OH)CH_2OH+2H^+ \quad (1a)$$

$$CH_3CH=CH_2+2H_2O-2e^- \rightarrow CH_3C(O)CH_3+2H^+ \quad (1a)$$

$$\tfrac{1}{2}O_2+2H^++2e^- \rightarrow H_2O \quad (2)$$

Figure 2:
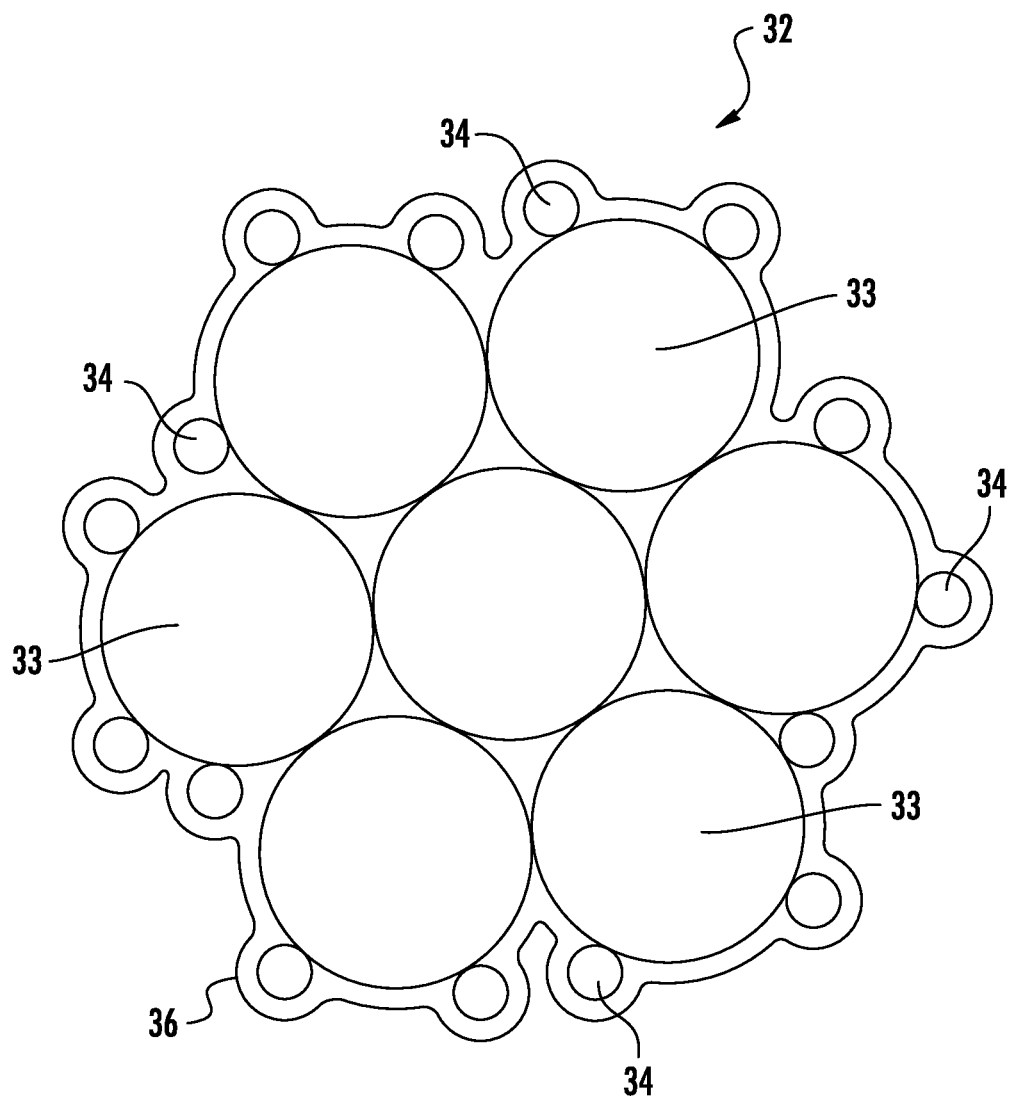
FIG. 2 depicts an exemplary illustration of nanoparticle catalyst supported on a catalyst support along with ion conducting medium such as an ionomer.

The precise composition of the electrodes, and materials used in fabricating them, will depend on the particular hydrocarbons being tested for and on design parameters for the sensor and other system components with which it is used. A variety of catalytic noble metals and their alloys (e.g., iridium, rhenium, palladium, platinum, copper, indium, rubidium, silver, gold) can be used to form the electrodes. In some exemplary embodiments, the sensing and/or counter electrodes comprise platinum or a binary or ternbary platinum alloys such as PtNi, PtFe, PtCo, PtRu, PtRuNi, PtCr, PtCoCr, PtIrCo, or PtCuFe, wherein the Pt content in atomic ratio ranges from 20% to 100%. In some palladium, or a mixture or alloy of platinum and palladium. In some exemplary embodiments, the sensing and/or counter electrodes comprise palladium or a palladium alloy such as PdAg, PdNi, PdCu, PdRu, or PdY. The counter electrode can comprise a catalyst comprising noble metal that is different from the sensing electrode catalyst metal(s). The catalysts in the counter electrode can be chosen to facilitate oxygen reduction reaction. Electrodes used in electrochemical sensors typically include an electrically conductive material in addition to the noble metal catalyst, and this is often provided by disposing nanoparticles of noble metal catalyst on larger particles of conductors such as carbon black, which is commonly referred to as a carbon-supported catalyst. However, for the detection of hydrocarbons involving oxidation of the hydrocarbons on the sensing electrode, the electrode potentials needed to effectively oxidize hydrocarbons such as olefins and substituted olefins (e.g., fluorinated olefins) exceed the thermodynamic oxidation of carbon support materials, (e.g, 207 mV vs. standard hydrogen electrode). Accordingly, the sensing electrode of the sensors described herein can comprise unsupported catalysts or catalysts supported on an oxidation-resistant support that is different from carbon black. For both unsupported catalyst and supported catalyst, the sensing electrode can be applied onto the solid polymer electrolyte by forming an ink comprising nanoparticles (by nanoparticles, it is meant that the particles have a nominal diameter of less than 20 nm, more specifically from 2-10 nm) and ionomer dispersed in a solvent mixture, and depositing a layer of the ink onto the surface of the solid polymer electrolyte membrane by screen printing, ink jet printing, or similar methods. After evaporation of the solvent, the resultant electrode is in the form of a layer having a composite structure comprising catalyst nanoparticles in an ionomer matrix, where the ionomer functions as a conductive matrix material having catalyst nanoparticles dispersed throughout. A second method to fabricate the MEA is to deposit the electrode ink onto a substrate, i.e. Teflon™ or Kapton™ sheet, to make a decal after solvent evaporation, followed by hot pressing to transfer the catalyst layer onto a membrane. In the case of a supported catalyst for the sensing electrode, the catalyst is supported on an oxidation-resistant conductive support, which can comprise oxidation-resistant support particles that are typically larger than the catalyst nanoparticles. In some exemplary embodiments, the support particles can have a nominal diameter of from 20 to 200 nm. A supported catalyst is depicted in FIG. 2, which depicts a portion of an agglomerate 32 having conductive support particles 33 with catalyst particles 34 disposed thereon, fully or partially covered by a thin layer of ionomer 36. By "oxidation-resistant, it is meant that at the operational positive voltage bias of the sensor (i.e., 100 to 400 mV), the material of the support particles produces a baseline signal that drifts less than $\tfrac{1}{5}^{th}$ of the signal generated by a test gas or refrigerant such as R1234ze. A stable baseline may exhibit a drift rate less than 0.48 µA/cm2/yr, or 0.011 µA/cm2/1000h. Examples of materials for the oxidation-resistant support in the sensing electrode include, but are not limited to graphitized carbon, carbon nanotubes (CNT), and conductive or semi-conductive metal oxides such as $TiO_2$, $WO_3$, $SnO_2$, etc. In another embodiment, the noble metal containing catalyst and conductive oxides can be co-loaded onto a support to achieve higher activity, for example Pt—$WO_3$/CNT. These conductive metal oxides can be undoped or they can be doped with metals such as Sb, V, Tl, Mn, Co, Fe, etc.

The counter electrode can also be formed from conventional carbon-supported catalyst with catalyst particles supported on larger carbon particles with conductive or nonconductive binders, i.e. Teflon™, and the current collector associated with the counter electrode can also be formed from a carbon screen, mesh, or felt. In an exemplary embodiment, the counter electrode can be formed from an agglomerate of a conductive carbon support particles with a nominal diameter of about 20-200 nm, with catalyst particles (nominal diameter of about 2-10 nm) disposed thereon, covered by a thin layer of binder (e.g., an ionomer such as Nafion® or a nonconductive binder).

The solid polymer electrolyte can be formed from any ionomer capable of conducting protons across the electrolyte membrane between the sensing electrode and counter electrode. Exemplary ionic polymers include ionic groups attached to a polymer so that the polymer has the ionic-exchange ability, such groups including but not limited to sulfonic acid, phosphonic acid, and sulfonimide acid. Exemplary ionomers include per-fluorinated sulfonic acid ("PFSA"), such as Nafion® ionomer and Solvey Solexis Auqivion™ ionomer, sulfonated polystyrene, sulfonated polysulfone, disulfonated poly(arylene ether sulfone) block-copolymers ("BPSH"). Conventional additives, e.g., surfactants, solvents (e.g., polyethylene glycol), and fine particles (such as functionalized of non-functionalized silica, carbon-based powders, metal-oxides particles) can also be added to the polymer matrix. The above-described ionomers for the solid polymer electrolyte can also be used as the ionomer for the electrodes.

In some embodiments, the solid polymer electrolyte and/or ionomer in the electrodes can be impregnated with a polar liquid such as an ionic liquid (i.e., a salt with its melting point near or below room temperature). In some embodiments, the membrane electrode assembly is free of water or is not impregnated with water, except for the presence of water that is electrochemically generated at the counter electrode by reaction (2) described above.

The sensor can be operated by applying a positive bias voltage to the sensing electrode relative to the counter electrode or a reference electrode, exposing the sensing electrode to the gas being tested, measuring voltage or current in an electrical circuit connecting the sensing electrode and the counter electrode, and converting the measured voltage or current to a reading indicative of the presence and/or concentration of the component in the gas being tested. Oxidation of hydrocarbons or substituted hydrocarbons at the sensing electrode will cause an electrochemical response that can be detected as voltage or current in the circuit. In some embodiments, the potentiostatic circuit, microprocessor, or similar device 19 is configured to apply the positive voltage bias and measure the response voltage or current. In some embodiments, the positive voltage bias applied to the sensing electrode relative to the counter electrode is from 20 mV to 800 mV. In some embodiments, the applied positive voltage bias can be applied as a constant positive voltage bias ranging from 200 mV to 400 mV. In some embodiments, the positive voltage bias can be varied within the 20 mV to 800 mV range by an amount of up to 400 mV.

The sensor can detect various hydrocarbons such as ethane, propane, and substituted hydrocarbons such as fluorinated hydrocarbons (e.g., difluoromethane or R32, 1,1-difluoroethane or R152a, 1,1,1,2-tetrafluoroethane or R134a) or chlorinated hydrocarbons (e.g., chloromethane or R40). Olefins, including fluoro-substituted olefins that offer low-ODP and low-GWP potential as well as good performance as refrigerants, can be difficult to detect using prior art sensors. In some embodiments, the sensors described herein are used to detect olefins such as propene. In some embodiments, the sensors described herein are used to detect substituted olefins such as fluoro-substituted olefins, e.g., any of the isomers of tetrafluoropropene (e.g., R1234ze, R1234yf, R1234zd).

Further description is provided in the following examples.

EXAMPLES

Figure 3:
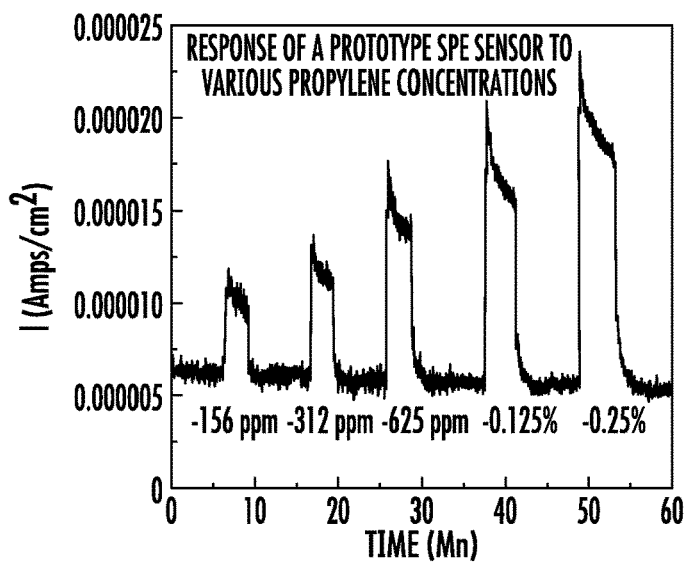
FIG. 3 depicts output of a sensor as described herein in response to exposure to propylene.
Figure 4:
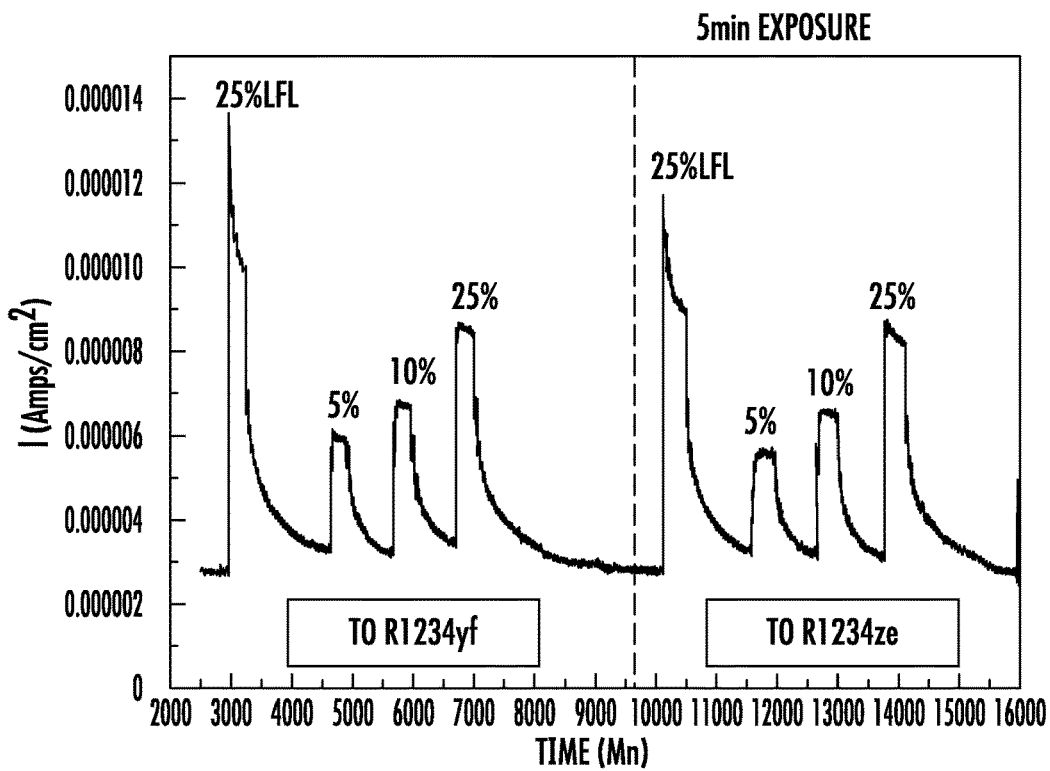
FIG. 4 depicts output of a sensor as described herein in response to exposure to 2,333-tetrafluoropropene (R1234yf) and trans-1,333-tetrafluoropropene (R1234ze) respectively.

A prototype sensor configured as shown in FIG. 1 without a reference electrode was operated with a positive voltage bias of 300 mV at the sensing electrode relative to the counter electrode and exposed to air, which was mixed periodically with varying concentrations of propylene. The sensor response is shown in FIG. 3. As shown in FIG. 3, the sensor effectively identified propene with a response that increased with increasing to propene concentration. In a separate test, the air was mixed periodically with varying concentrations of R234yf or R1234ze. The sensor response is shown in FIG. 4, which shows that the sensor effectively identified the compounds with a response that increased with increasing concentration.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the spirit and scope of the present disclosure. Additionally, while various embodiments of the present disclosure have been described, it is to be understood that aspects of the present disclosure may include only some of the described embodiments. Accordingly, the present disclosure is not to be seen as limited by the foregoing description, but is only limited by the scope of the appended claims.

The invention claimed is:

1. A method of testing for hydrocarbons or substituted hydrocarbons, comprising:
   providing a sensor comprising:
      a housing;
      a membrane electrode assembly disposed in the housing, the membrane electrode assembly comprising a sensing electrode comprising a first catalyst comprising noble metal nanoparticles, a counter electrode comprising a second catalyst comprising noble metal nanoparticles, and a solid polymer electrolyte disposed between the sensing electrode and the counter electrode, wherein the nanoparticles of the first catalyst are unsupported;
      a first current collector in electrical contact with the sensing electrode;
      a second current collector in electrical contact with the counter electrode;

the housing including an opening in fluid communication with the sensing electrode for test gas to contact the sensing electrode; and an electrical circuit connecting the sensing electrode and the counter electrode, applying a positive bias voltage to the sensing electrode relative to the counter electrode, introducing a test gas in communication with a source of hydrocarbons or substituted hydrocarbons into contact with the sensing electrode, and measuring voltage or current in the electrical circuit connecting the sensing electrode and the counter electrode to detect an electrochemical response from oxidation of hydrocarbons or substituted hydrocarbons at the sensing electrode.

2. The method of claim 1, wherein either or both of the first and second catalysts comprises platinum or a binary or a ternary platinum alloy.

3. The method of claim 2, wherein either or both of the first and second catalysts comprises PtNi, PtFe, PtCo, PtRu, PtRuNi, PtCr, PtCoCr, PtIrCo or PtCuFe, wherein the Pt content in atomic ratio ranges from 20% to 100%.

4. The method of claim 1, wherein either or both of the first and second catalysts comprises palladium or a palladium alloy.

5. The method of claim 4, wherein either or both of the first and second catalysts comprises PdAg, PdNi, PdCu, PdRu, or PdY, wherein the Pd content in atomic ratio ranges from 30% to 100%.

6. The method of claim 1, wherein either or both of the sensing electrode and the counter electrode further comprise an ionomer.

7. The method of claim 1, wherein the first current collector comprises stainless steel, or the second current collector comprises carbon, or the first current collector comprises stainless steel and the second current collector comprises carbon.

8. The method of claim 1, wherein the first current collector, the second current collector, or each of the first current collector and the second current collector also functions as a gas diffusion medium.

9. The method of claim 1, further comprising a reference electrode in electrical contact with the solid polymer electrolyte.

10. The method of claim 1, wherein the concentrations of hydrocarbons or substituted hydrocarbons are determined according to the electrical signal generated by the sensor.

11. The method of claim 1, wherein the positive bias voltage is from 20 mV to 800 mV.

12. The method of claim 11, wherein a constant positive bias voltage is applied, ranging from 200 mV to 400 mV.

13. The method of claim 11, wherein the positive bias voltage is varied within a range up to 400 mV.

14. A method of testing for olefins or substituted olefins, comprising:

providing a sensor comprising:

a housing;

a membrane electrode assembly disposed in the housing, the membrane electrode assembly comprising a sensing electrode comprising a first catalyst comprising noble metal nanoparticles, a counter electrode comprising a second catalyst comprising noble metal nanoparticles, and a solid polymer electrolyte disposed between the sensing electrode and the counter electrode, wherein the nanoparticles of the first catalyst are unsupported;

a first current collector in electrical contact with the sensing electrode;

a second current collector in electrical contact with the counter electrode;

the housing including an opening in fluid communication with the sensing electrode for test gas to contact the sensing electrode; and an electrical circuit connecting the sensing electrode and the counter electrode, applying a positive bias voltage to the sensing electrode relative to the counter electrode, introducing a test gas in communication with a source of olefins or substituted olefins into contact with the sensing electrode, and measuring voltage or current in the electrical circuit connecting the sensing electrode and the counter electrode to detect an electrochemical response from oxidation of hydrocarbons or substituted hydrocarbons at the sensing electrode.

15. The method of claim 14, wherein the olefins or substituted olefins comprise fluoro-substituted olefins.

16. The method of claim 15, wherein the fluoro-substituted olefins comprise one or more isomers of tetrafluoropropene.

* * * * *